(12) United States Patent
Deem et al.

(10) Patent No.: US 8,070,670 B2
(45) Date of Patent: Dec. 6, 2011

(54) METHODS AND DEVICES FOR LUMINAL AND SPHINCTER AUGMENTATION

(75) Inventors: Mark E. Deem, Mountain View, CA (US); Hanson S. Gifford, III, Woodside, CA (US); Bernard Andreas, Redwood City, CA (US); Sunmi Chew, San Jose, CA (US); Ron French, Santa Clara, CA (US); Doug Sutton, Pacifica, CA (US)

(73) Assignee: Torax Medical, Inc., Maple Grove, MN (US)

( * ) Notice: Subject to any disclaimer, the term of this patent is extended or adjusted under 35 U.S.C. 154(b) by 0 days.

(21) Appl. No.: 11/560,776

(22) Filed: Nov. 16, 2006

(65) Prior Publication Data
US 2007/0129597 A1    Jun. 7, 2007

Related U.S. Application Data

(63) Continuation of application No. 10/612,325, filed on Jul. 1, 2003, now Pat. No. 7,175,589.

(60) Provisional application No. 60/393,624, filed on Jul. 2, 2002.

(51) Int. Cl.
*A61F 2/02* (2006.01)
(52) U.S. Cl. .......................................................... 600/30
(58) Field of Classification Search ............... 600/29–32, 600/12, 9, 37; 128/885, 899, 897; 623/4.1
See application file for complete search history.

(56) References Cited

U.S. PATENT DOCUMENTS

| | | | |
|---|---|---|---|
| 3,731,670 A * | 5/1973 | Loe ................................ | 600/30 |
| 4,005,699 A | 2/1977 | Bucalo | |
| 4,024,855 A * | 5/1977 | Bucalo ............................ | 600/30 |
| 4,643,169 A | 2/1987 | Koss et al. | |
| 4,978,323 A | 12/1990 | Freedman | |
| 4,994,019 A * | 2/1991 | Fernandez et al. ............... | 600/30 |
| 5,451,406 A | 9/1995 | Lawin et al. | |
| 5,509,888 A | 4/1996 | Miller | |
| 6,234,973 B1 * | 5/2001 | Meador et al. ................. | 600/486 |
| 6,348,033 B1 * | 2/2002 | Catlett ............................ | 600/15 |
| 6,470,892 B1 | 10/2002 | Forsell | |
| 6,511,508 B1 * | 1/2003 | Shahinpoor et al. ........... | 623/4.1 |
| 6,604,529 B2 | 8/2003 | Kim | |
| 6,730,014 B2 | 5/2004 | Wilk | |
| 7,468,060 B2 | 12/2008 | Utley et al. | |
| 2002/0028979 A1 | 3/2002 | Silverman et al. | |
| 2002/0091295 A1 | 7/2002 | Wilk | |
| 2003/0139808 A1 | 7/2003 | Shahinpoor et al. | |
| 2003/0153806 A1 | 8/2003 | Miller | |
| 2004/0147801 A1 | 7/2004 | Kugler et al. | |

FOREIGN PATENT DOCUMENTS

| | | |
|---|---|---|
| DE | 30 11 742 | 10/1981 |
| DE | 30 11 742 A1 | 10/1981 |
| DE | 31 39 811 | 4/1983 |
| JP | 58-8323 U | 1/1983 |
| WO | WO 98/56302 | 12/1998 |
| WO | WO 01/26588 A2 | 4/2001 |
| WO | WO 02/11696 A2 | 2/2002 |

* cited by examiner

*Primary Examiner* — Charles A Marmor, II
*Assistant Examiner* — Christine Hopkins
(74) *Attorney, Agent, or Firm* — Ropes & Gray LLP; Jeffrey H. Ingerman

(57) ABSTRACT

Devices and methods for augmenting or otherwise enhancing closure of body lumens comprise magnetic or magnetizable components or particles which are implanted in the wall of the lumen. The magnet fields exerted by the components or particles act to close the body lumen with a desired force.

12 Claims, 4 Drawing Sheets

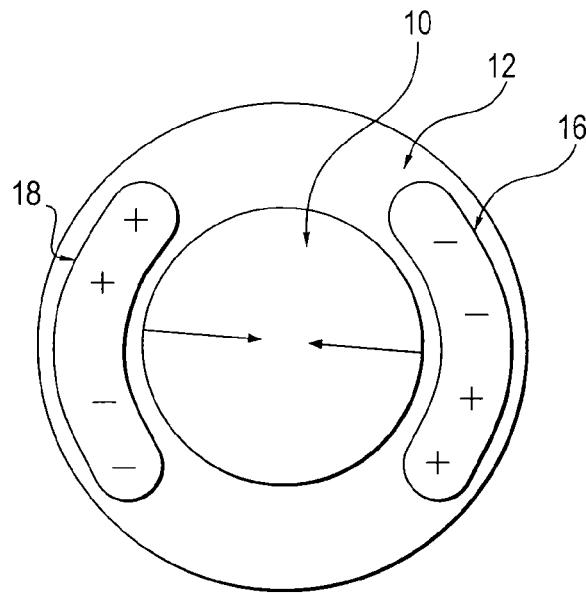
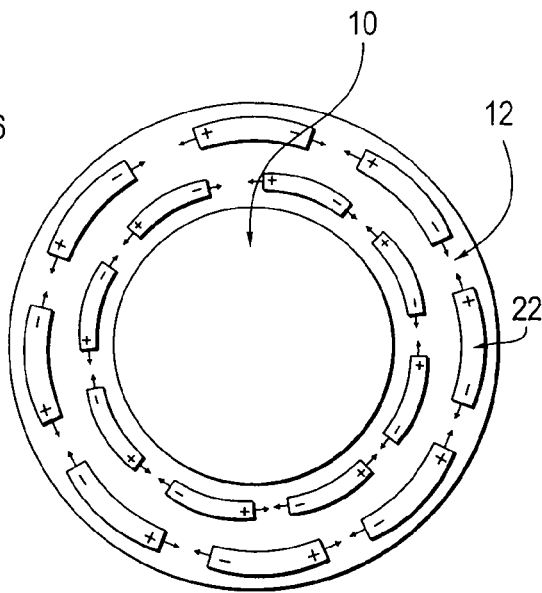
FIG. 1a    FIG. 1b
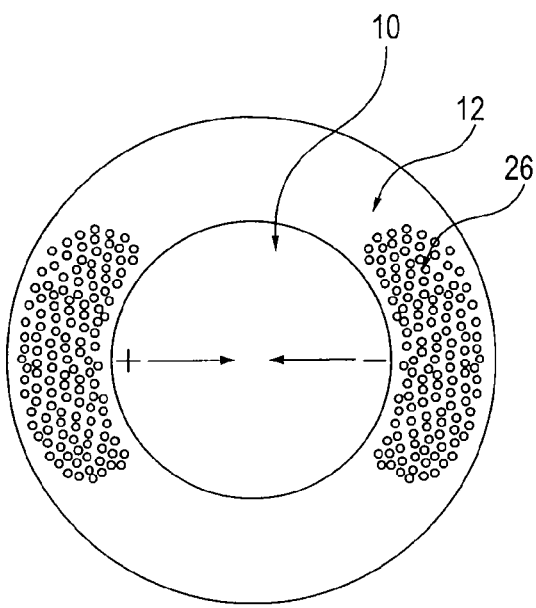
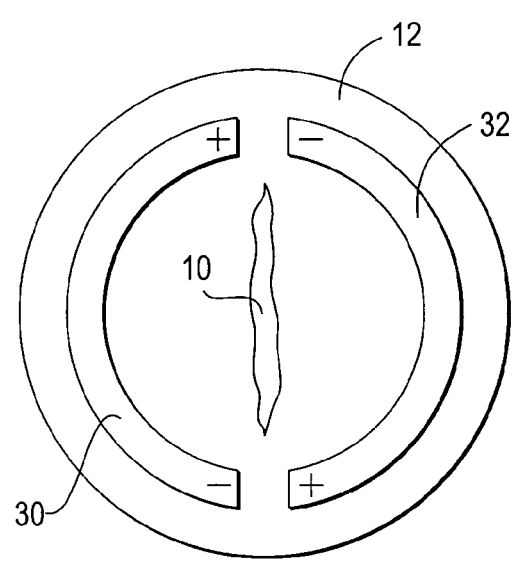
FIG. 1c    FIG. 1d

METHODS AND DEVICES FOR LUMINAL AND SPHINCTER AUGMENTATION

CROSS-REFERENCES TO RELATED APPLICATIONS

The present application is a continuation of U.S. application Ser. No. 10/612,325, filed Jul. 1, 2003 now U.S. Pat. No. 7,175,589, which is a non-provisional of U.S. Patent Application Ser. No. 60/393,624, filed Jul. 2, 2002, the full disclosures of which are incorporated herein by reference.

BACKGROUND OF THE INVENTION

The present invention generally relates to methods and devices for medical or surgical therapy. More particularly, the invention relates to methods and devices for augmenting a sphincter, such as the lower esophageal sphincter, or body lumens, such as the female urethra.

A variety of human ailments arise from the weakening of tissues surrounding body lumens and cavities due to disease, trauma, advancing age, or combinations of these causes. Of particular interest to the present invention, a condition known as gastroesophageal reflux disease or "GERD," arises when the lower esophageal sphincter ("LES") weakens and permits the contents of the stomach to move back into the esophagus. Similarly, fecal incontinence can occur when the anal sphincter becomes weakened and ceases to function properly. Female urinary incontinence can occur with weakening of the urethra which is responsible for containing the contents of the bladder. Male urinary incontinence arises with damage to the urinary sphincter. The outlet of the stomach is controlled by the pyloric sphincter. Decreased muscle tone in the pyloric sphincter can lead to rapid gastric emptying which can cause digestive distress.

The human gastrointestinal tract begins at the mouth, and includes the pharynx, esophagus, stomach, small and large intestines, and rectum. Small, ring-like muscles, called sphincters, surround portions of the gastrointestinal tract. In a healthy person, these muscles contract in a coordinated fashion during eating and digestion to temporarily separate one region of the alimentary canal from an other. One example of a gastrointestinal sphincter is the anal sphincter, which provides fecal continence. Another example is the muscular ring called the lower esophageal sphincter ("LES"), which surrounds the opening between the esophagus and the stomach.

Normally, the LES relaxes to allow food to pass from the esophagus to the stomach and contracts to prevent food in the stomach from refluxing backwards into the esophagus. Stomach muscles churn food and digestive juices into a mass called chyme. The muscles then squeeze the chyme toward the opposite, intestinal end of the stomach by peristaltic waves, which start at the top of the stomach and move downward. The pyloric sphincter, another ring-like muscle, eventually relaxes to allow stomach contents to enter the first part of the small intestine. If the LES does not contract properly, however, chyme and other stomach contents may be pushed back into the esophagus causing the painful symptom of heartburn and, potentially permanent damage to the esophageal wall. This insufficiency of the LES, accompanied by regurgitation of stomach contents into the esophagus, is commonly referred to as gastroesophageal reflux disease, or "GERD."

Gastrointestinal reflux disease is a common disorder, with an estimated two percent of the adult population suffering from the syndrome. The incidence of GERD increases markedly after the age of 40, and it is not uncommon for patients experiencing symptoms to wait years before seeking medical treatment. Postponing treatment can lead to further health concerns, as continued presence of acid in the esophagus may lead to permanent damage of the esophagus. It has also been hypothesized that such esophageal damage may be a precursor to esophageal cancer.

Generally, many factors are thought to potentially contribute to the occurrence of GERD. For example, transient LES relaxation, decreased LES resting tone, impaired esophageal clearance, delayed gastric emptying, decreased salivation, and impaired tissue resistance all may contribute to causing GERD. Lifestyle factors may also contribute to cause reflux. Smoking, large meals, fatty foods, caffeine, pregnancy, obesity, body position, drugs, hormones, and paraplegia may all exacerbate GERD. Also, hiatal hernias frequently accompany severe cases of GIERD.

In addition to heartburn, other frequently reported symptoms of GERD include painful swallowing, difficulty swallowing, pulmonary symptoms such as coughing, wheezing, asthma, aspiration pneumonia, and interstitial fibrosis, oral symptoms such as tooth enamel decay, gingivitis, and halitosis, throat symptoms such as a soreness, laryngitis, hoarseness, and a globus sensation; and earache. As mentioned briefly above, complications of GERD include esophageal damages, such as erosion, esophageal ulcer, and esophageal stricture; replacement of normal esophageal epithelium with abnormal (Barrett's) epithelium; and pulmonary aspiration. Barrett's epithelium, in turn, may be a precursor to esophageal cancer.

Currently available therapies for treatment of GERD generally focus on pharmaceutical therapy and surgery. Drug therapies typically reduce or block stomach acid secretions, but do not strengthen or otherwise treat the LES. Surgical intervention typically includes procedures which attempt to create a sphincter-like mechanism at the site of the LES. Nissen fundoplication, for example, is an abdominal surgery that involves freeing a portion of the stomach from surrounding connective tissue, wrapping it around the outside of the esophagus at approximately the location of the LES, and attaching it back to another part of the stomach. Although this procedure often successfully tightens the esophagus at an area near the LES and may succeed in preventing GERD, it is often difficult to gauge how tight or loose to wrap the stomach—if wrapped too tightly, food has difficulty passing into the stomach, if wrapped too loosely, GERD will not be prevented.

Thus, GERD is a very prevalent condition with numerous painful symptoms, potentially serious complications, and relatively few viable treatment options. Therefore, it would be advantageous to have methods and devices to augment the LES to prevent or treat GERD. Ideally, such methods and devices would provide for long-lasting or even permanent treatment of the LES in a non-invasive or minimally invasive manner. Additionally, it would be beneficial if such methods and devices could be used in treating other body sphincters, such as the anal sphincter to treat fecal incontinence.

Urinary incontinence arises in both men and women with varying degrees of severity and from different causes. In men, the condition frequently occurs as a result of prostatectomies which damage the urinary sphincter. In women, the condition typically arises after pregnancy where stretching of the structure supporting the urinary tract can weaken the urethra.

A number of approaches have been developed for treating urinary incontinence. Of particular interest to the present invention, techniques have been developed for injecting collagen or other bulking agents into tissues surrounding the urethra in women and the urinary sphincter in men. While these treatments are at least partly successful, it would be beneficial to provide alternative treatments. Bulking agents, such as collagen, are resorbed and thus provide only temporary relief. Most persistent and substantial bulking agents can evert the sphincter and prevent its normal functioning.

Thus, it would be desirable to provide methods and systems for bulking or toning the sphincter. In particular, it would be desirable to be able to augment the sphincter sufficiently to keep the sphincter closed until sufficient force is applied to open the sphincter, at which point the closing force would drop off significantly. Similarly, with urinary incontinence, present bulking agents will cause closing of the urinary tract before the bladder has completely emptied. An approach which allowed the urinary tract to remain open longer would be beneficial. The present invention can at least partly meet these goals by providing a bulking or closing force which, once a lumen is opened, drops off rapidly to allow the lumen to remain open until opening forces fall to a very low point.

BRIEF DESCRIPTION OF THE DRAWINGS

FIGS. 1a-1d are cross-sectional views on an esophagus from the perspective designated by arrows A in FIG. 1, showing multiple embodiments of magnetic devices for augmentation of the lower esophageal sphincter, according to various embodiments of the invention.

DETAILED DESCRIPTION OF THE INVENTION

Generally, the present invention provides devices and methods for treating sphincters in human bodies. More specifically, the invention includes devices and methods that augment sphincters by implanting, injecting, or otherwise positioning two or more magnetic devices within a wall of the sphincter. Through magnetic attraction, between the two or more devices, the tone of the treated sphincter is increased.

Although many embodiments will be configured for treatment of the lower esophageal sphincter ("LES"), and although the following description focuses on that application, other embodiments may be used to treat any other suitable sphincter in a body. In some embodiments, for example, methods and devices of the present invention may be used to augment the anal sphincter, for example to treat fecal incontinence. Therefore, the following description is provided for exemplary purposes only and should not be construed to limit the scope of the invention.

It should also be emphasized that the term "magnetic device," for the purposes of this application, means any suitable device or material which may have, or be charged with, magnetic energy. For example, in some embodiments a magnetic device may include two magnets with opposite polarities that attract one another. In other embodiments, a magnetic device may include two pieces of a ferrous or other magnetizable material that do not have charges. These non-charged materials may be inserted into an area of the body and then a magnetizing device may be used to magnetize the materials. Thus, "magnetic device" generally means any device or material which is magnetized or magnetizable.

Figure 1:
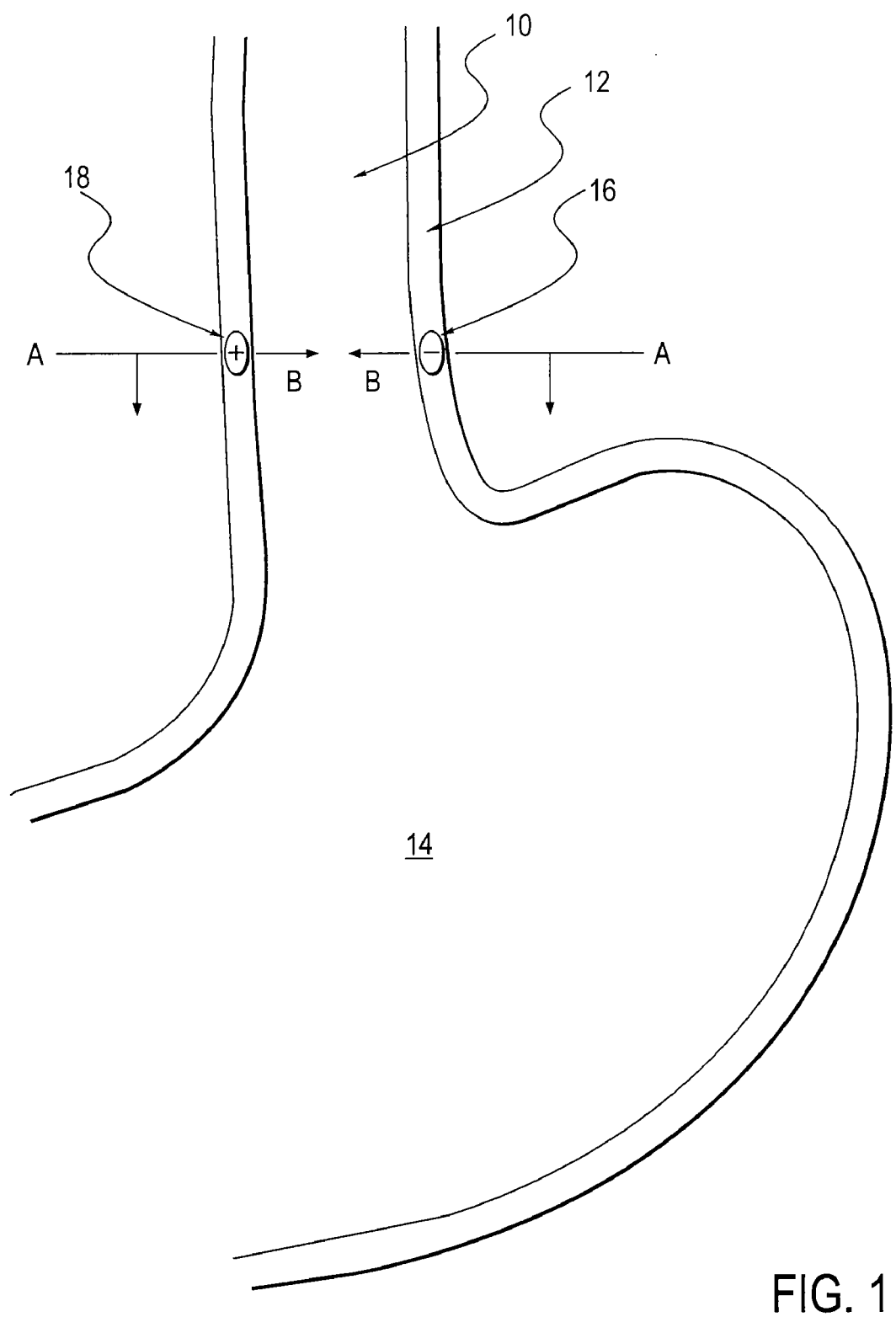
FIG. 1 is a frontal, cross-sectional view of an esophagus and stomach, with magnetic devices positioned in the wall of the esophagus to augment the lower esophageal sphincter in accordance with an embodiment of the invention.

Referring now to FIG. 1, an esophagus with an esophageal lumen 10 and an esophageal wall 12 are shown leading into a stomach 14. In accordance with one embodiment of the invention, two magnetic devices 16, 18 have been implanted in the wall 12 at a location at or near the LES. Through their attractive force, shown by arrows B, magnetic devices 16, 18 augment the LES by increasing the tone of wall 12, or in other words by partially constricting lumen 10 of the esophagus.

Generally, magnetic devices 16, 18 may include any material or combination of material which has magnetic properties or is magnetizable. Magnetic devices 16, 18 will also be compatible with the tissue in which they are placed, so that adverse reactions to the devices are avoided. In some embodiments, for example, a suitable ferrous material or rare earth metal may be used and that material may be coated in a biocompatible metal such as stainless steel, platinum, polymer, or pyrolytic carbon. Any suitable sizes, shapes and magnetic powers of magnetic devices 16, 18 may be used and such sizes, shapes and powers will typically be based on the anatomy of the patient, the degree with which the LES is desired to be augmented and the like. In some embodiments, magnetic devices 16, 18 may be magnetized, and/or their magnetic powers may be adjusted, after the devices 16, 18 are placed in the wall 12. This magnetization and/or adjustment may be accomplished by use of any suitable device, such as an endoscope with a powerful magnet at its distal end, which may be positioned near magnetic devices 16, 18.

Referring now to FIG. 1a, magnetic devices 16, 18 may have any of a number of suitable configurations. In one embodiment, the devices 16, 18 are magnets arranged to have their oppositely charged poles placed at generally opposed locations across esophageal lumen 10 within esophageal wall 12. The attraction between the two oppositely charged, oppositely positioned devices 16, 18 increases the tone of, and pressure within, the esophagus, thus helping to augment the natural function of the LES.

In another embodiment, as in FIG. 1b, multiple magnets 22 may be positioned in the wall 12 of the esophagus in a radial pattern. The magnets 22 may attract each other in a radial configuration such that they pull together, thus also increasing tone and pressure in the esophagus. Multiple magnets 22 as in FIG. 1b may be placed within the esophageal wall 12 as separate pieces of material, for example they may be placed between muscular layers of the wall 12. In other embodiments, the magnets 22 may be contained within a retaining ring to keep then aligned in an approximately radial configuration. Such a ring may be made of any suitable material, such as a polymeric mesh.

Referring now to FIG. 1c, yet another embodiment uses magnetic or magnetable particles 26 to augment the LES. As with embodiments incorporating multiple magnets 22, when magnetic particles 26 are used they may be contained in a retaining ring, sac, or other device or may be injected or implanted separately into the wall 12 of the esophagus. In some embodiments, for example, magnetic particles 26 may be injected into an area formed between two muscle layers of the esophageal wall 12. Such an area may form a pocket for holding the magnetic particles 26 in place. Magnetic particles 26 may be placed in two or more locations in the esophageal wall 12, in various embodiments. For example, in FIG. 1c magnetic particles 26 are shown in two, generally opposite, locations in the wall 12 and are oppositely charged so as to attract one another across the esophageal lumen 10. In other embodiments, magnetic particles 26 may be injected or placed into three, four, five or more pockets and may have magnetic charge configurations which cause a radial attraction pattern as described in FIG. 1b with multiple magnets 22.

When employing particles as illustrated in FIG. 1c, it may be difficult to properly arrange the particles orientation so that the magnetic fields on each side of the esophagus are disposed with opposed opposite polarities. Thus, it will usually be preferred to initially inject or otherwise introduce the particles prior to magnetization. Usually, the particles will be composed of a ferrous metal coated with a suitable biocompatible coating as described above, preferably pyrolytic carbon. After the particles are injected on at least one side of the esophagus, the particles will be exposed to a magnetizing field, usually an internally or externally positioned electromagnet having an appropriate field strength, in order to provide for a desired magnetization. It will be appreciated that while each individual particle will become magnetized, the particles together will collectively act as a single large magnet having poles at opposite ends. Usually, a second set of magnetic particles will then be introduced on the other side of the esophagus. Because of the difficulty in orienting a magnetic field in the second group of particles, the second group will optionally be left unmagnetized. So long as the second particles, which will usually also be composed of a ferrous metal coated with pyrolytic carbon, are magnetic (as opposed to magnetized), they will be attracted by the magnetic field exerted by the first group of particles.

In situ magnetization also allows for adjustment of the magnetic field induced in the particles (or in a larger bar or other magnets for that matter) after testing. For example, the augmented sphincter can be exposed to pressure in an effort to cause reflux. If reflux occurs at unacceptably low pressures, the magnetic particles can be further magnetized, taking care to isolate the second group of particles if they are not to be magnetized. Alternatively, the patient may be followed-up to see if the first treatment has sufficiently resolved the problem. If not, the particles can be further magnetized in order to provide for additional augmentation.

Referring now to FIG. 1d, C-shaped magnets 30 and 32 can be implanted on opposite sides of the LES or elsewhere in the esophagus. The particular C-shaped geometry of the magnets 30 and 32 is selected so that they will exert a continuous closing force on the esophageal lumen 10 to inhibit reflux, but will always leave an open area therebetween so that the lumen can still open when needed for swallowing. Moreover, the risk of injuring the tissue of the esophageal wall is reduced. In other embodiments, the lumen would close but with a significantly reduced force so that tissue would not be crushed.

Figure 2:
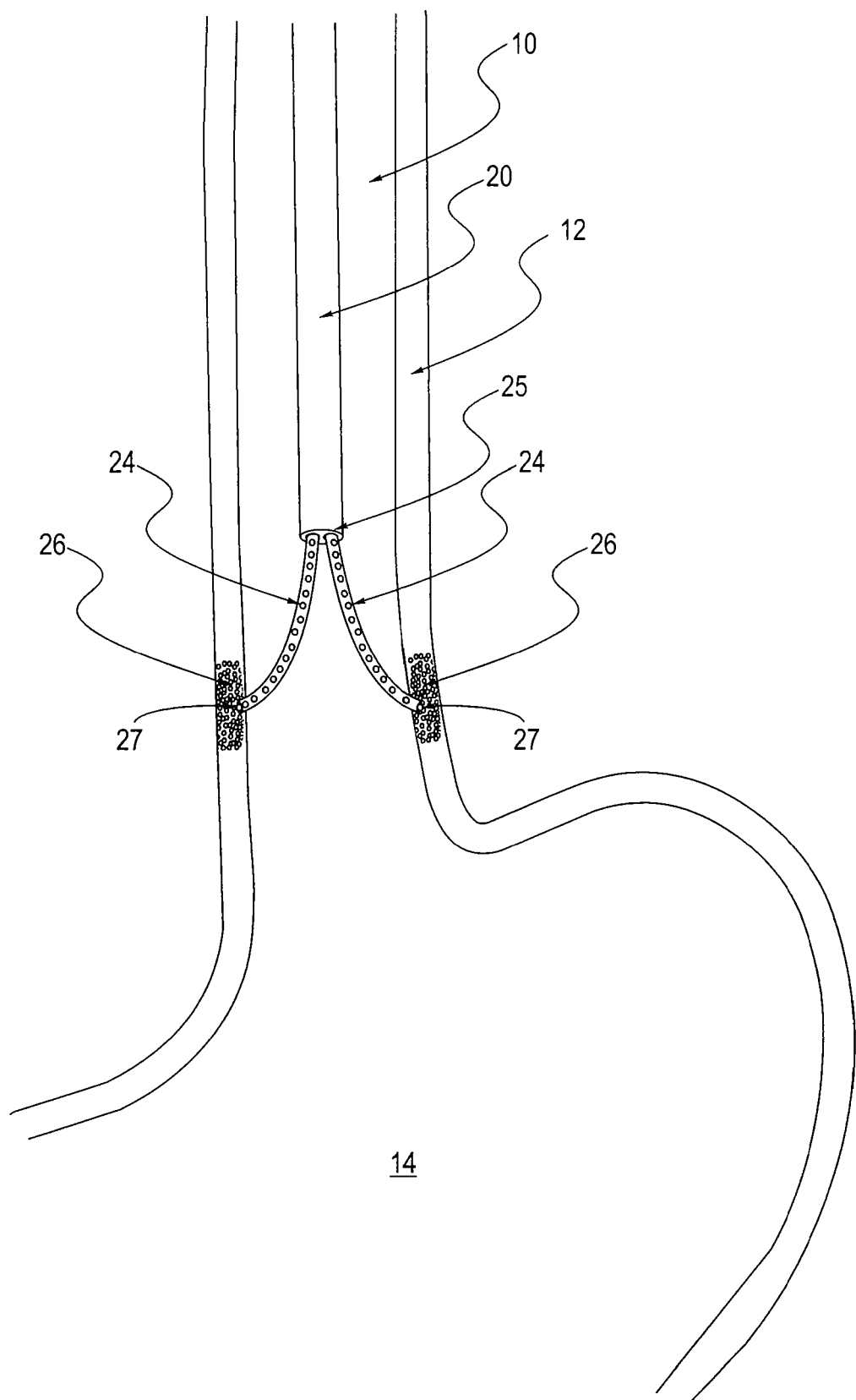
FIG. 2 is a frontal, cross-sectional view of an esophagus and stomach, with magnetic particles being placed in the wall of the esophagus by a magnet delivery device to augment the lower esophageal sphincter according to an embodiment of the invention.

Referring now to FIG. 2, magnetic devices 16, 18, 22, 26 may be placed within the esophageal wall by any suitable means. For example, in some embodiments the devices may be placed via minimally invasive surgical techniques such as laparoscopic or robot surgery. In other embodiments, the devices may be placed via an endoscope inserted through a patient's mouth and into the patient's esophagus. Actual insertion of magnetic devices may also be accomplished by any suitable means. For example, in some embodiments the magnetic materials may be injected into esophageal wall 12, such as with a device including a distal needle and an injection system. In other embodiments, one or more incisions may be made in the esophageal wall 12 and the magnetic devices may be inserted through the incisions.

FIG. 2 shows one embodiment of a device for delivering magnetic particles 26 to an esophageal wall 12. Generally, the device includes a catheter 20 with proximal (not shown) and distal 25 ends and multiple delivery tubes 24 with proximal (not shown) and distal 27 ends. The delivery tubes 24 protrude from the distal end 25 of the catheter 20 to deliver the magnetic particles 26. In some embodiments, each of the distal ends 27 of the delivery tubes 24 includes a needle for piercing the wall 12 of the esophagus. Although two delivery tubes 24 are shown in FIG. 2, other embodiments of a delivery device may include one tube or more than two tubes. The use of a single tube may be preferred when the particles are sequentially delivered to two or more locations with magnetization of only certain ones of the particle sites. Additionally, the tubes 24 may have any suitable combination of sizes, lengths, diameters and configurations. In one embodiment, for example, the inner diameter or each tube 24 is only slightly larger than the outer diameter of each magnetic particle 26, such that the particles 26 are delivered generally in a single file line. Such a configuration may allow for more controlled delivery of magnetic particles to a treatment location within the wall 12 of the esophagus.

Other devices for delivering magnetic devices may include one or more different features from those shown in FIG. 2. For example, some embodiments may include an endoscope with an incising device and a grasping and releasing device for incising the esophageal wall 12 and implanting a magnetic device. Other embodiments may include a magnetization device for magnetizing materials placed in the esophageal wall 12. Still other embodiments may include an adjustment mechanism for adjusting the powers of one or more magnetic devices. Generally, any suitable combination of delivery devices for delivering magnetic devices into a sphincter, whether incorporated into an endoscope device or otherwise provided, is contemplated within the scope of the invention.

In one embodiment, a method for augmenting an LES suitably includes first introducing a magnet delivery device into a mouth of a patient and advancing the device into the esophagus of the patient. The distal end of the device may then be positioned in a location within the lumen of the esophagus for delivering magnetic devices. Typically, this location will be at or near the LES. A delivery mechanism of the delivery device may then be used to inject, implant, or otherwise position the magnetic devices within the wall of the esophagus, in any suitable location to augment the LES. In some cases, a pressure sensing device such as a pressure sensing endoscope or catheter is then placed into the esophagus to measure the pressure in the lumen of the esophagus in a location at or near the LES. If the pressure approximates a desired pressure, then the procedure may be complete. On the other hand, if an adjustment is desired to be made to the pressure, a magnet or other magnetizing device may be inserted and positioned to increase or decrease the magnetic power of the implanted devices. In other embodiments, as described above, the implanted devices may have no magnetic power when placed in the esophageal wall and may be magnetized by a magnetizing device. In some embodiments, an adjustment device may be used at a later date to increase or decrease the magnetic power of the implanted devices to more suitably augment the LES to treat GERD or other conditions of the esophagus.

Figure 3:
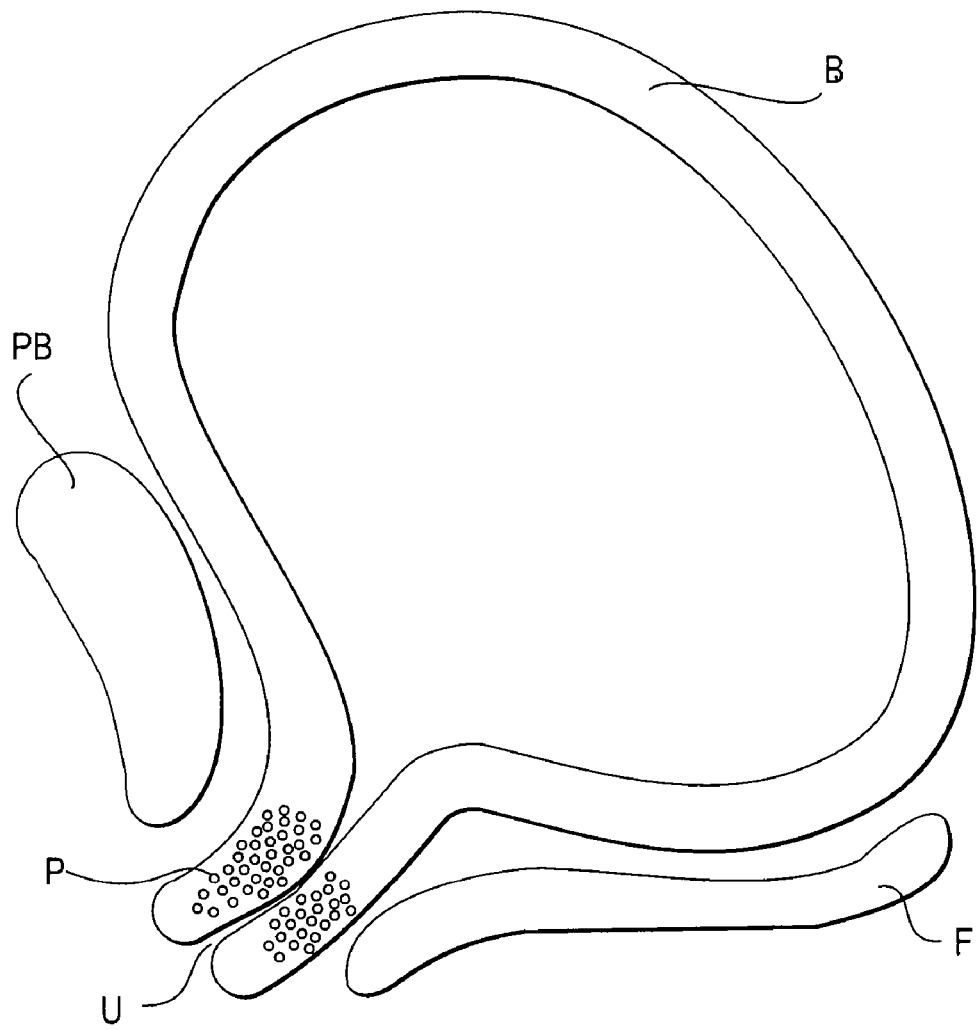
FIG. 3 is a schematic illustration of a female urethra which has been augmented with magnetic and/or magnetized particles according to the methods of the present invention.

Referring now to FIG. 3, female urinary incontinence may be treated by the methods and with the apparatus of the present invention generally as described above with respect to treating the LES. Particles P may be injected onto opposite sides of the urethra U disposed between the facia F and pubic bone PB. Particles may be injected in one, two, or more stages using a catheter introduced into the urethra in a manner similar to that described above with respect to the esophagus. Usually, the particles will be introduced prior to magnetization, with only the particles on one side of the urethra eventually being magnetized. Other aspects of the present invention described above will apply equally well to treatment of the urethra for inhibiting female urinary incontinence.

Although the foregoing is a complete and accurate description of the invention, various changes or additions may be made to various embodiments without departing from the scope of the invention as set forth in the appended claims. For example, various additional materials or combinations of materials may be used as magnetic devices, different embodiments of magnet delivery devices may be used, and or the like. Therefore, the detailed description above should not be construed to limit the scope of the present invention as it is defined by the appended claims.

What is claimed is:

1. Apparatus for urging tissue in a patient's body toward a closed position comprising:
   a plurality of more than two permanent magnets adapted for implanting in the patient in an annular array around the tissue; and
   a retaining structure adapted for implanting in the patient around said tissue for keeping all of the magnets aligned in the array such that each of the magnets occupies a respective segment of a circumference of the array and has its magnetic axis (1) lying in a plane in which the array lies, (2) extending along the circumference of the array, and (3) oriented so that each magnet continuously magnetically attracts the next adjacent magnets in the array.

2. The apparatus defined in claim 1 wherein the retaining structure limits distance that adjacent magnets in the array can move from each other.

3. Prosthetic apparatus for implanting in a patient's body to urge tissue in the body toward a closed position comprising:
   a plurality of more than two permanent magnets adapted for implanting in an annular array around the tissue; and
   means for keeping the magnets' positions in the array with each magnet occupying a respective segment of a circumference of the array and having its magnetic axis (1) extending along the circumference of the array, (2) lying in a plane in which the array lies, and (3) oriented so that each magnet continuously magnetically attracts the next adjacent magnets in the array.

4. The apparatus defined in claim 3 wherein the means for keeping allows adjacent magnets in the array to move toward or away from one another in a direction that is circumferential of the array while the means for keeping is keeping each magnet occupying a respective segment of a circumference of the array and having its magnetic axis (1) extending along the circumference of the array, (2) lying in a plane in which the array lies, and (3) oriented so that each magnet continuously magnetically attracts the next adjacent magnets in the array.

5. Prosthetic apparatus for implanting in a patient's body to urge tissue in the body toward a closed position comprising:
   a plurality of more than two permanent magnets adapted for implanting in an annular array around the tissue; and
   retaining structure that keeps each magnet at a respective position in the array with the magnetic axis of that magnet (1) lying in a plane in which the array lies, (2) aligned along a circumference of the array at that position, and (3) oriented so that each magnet continuously magnetically attracts the next adjacent magnets in the array.

6. The apparatus defined in claim 5 wherein the retaining structure allows adjacent magnets in the array to move toward or away from one another in a direction that is annular of the array while the retaining structure keeps each magnet at a respective position in the array with the magnetic axis of that magnet (1) lying in a plane in which the array lies, (2) aligned along a circumference of the array at that position, and (3) oriented so that each magnet continuously magnetically attracts the next adjacent magnets in the array.

7. Apparatus for urging tissue in a patient's body toward a closed position comprising:
   a plurality of more than two magnets adapted for implanting in the patient in an annular array around the tissue; and
   a retaining structure adapted for implanting in the patient around said tissue for keeping all of the magnets aligned in the array such that each of the magnets occupies a respective segment of a circumference of the array and has its magnetic axis (1) lying in a plane in which the array lies, (2) extending along the circumference of the array, and (3) oriented so that each magnet continuously magnetically attracts the next adjacent magnets in the array, until force is applied to urge the tissue toward an open position.

8. Prosthetic apparatus for implanting in a patient's body to urge tissue in the body toward a closed position comprising:
   a plurality of more than two magnets adapted for implanting in an annular array around the tissue; and
   means for keeping the magnets' positions in the array with each magnet occupying a respective segment of a circumference of the array and having its magnetic axis (1) extending along the circumference of the array, (2) lying in a plane in which the array lies, and (3) oriented so that each magnet continuously magnetically attracts the next adjacent magnets in the array, until force is applied to urge the tissue toward an open position.

9. Prosthetic apparatus for implanting in a patient's body to urge tissue in the body toward a closed position comprising:
   a plurality of more than two permanent magnets adapted for implanting in an annular array around the tissue; and
   retaining structure that keeps each magnet at a respective position in the array with the magnetic axis of that magnet (1) lying in a plane in which the array lies, (2) aligned along a circumference of the array at that position, and (3) oriented so that each magnet continuously magnetically attracts the next adjacent magnets in the array, until force is applied to urge the tissue toward an open position.

10. Apparatus for urging a lumen in a patient's body toward a closed position comprising:
    a plurality of more than two permanent magnets adapted for implanting in the patient in an annular array around the lumen; and
    a retaining structure adapted for implanting in the patient around said lumen for keeping all of the magnets aligned in the array such that each of the magnets occupies a respective segment of a circumference of the array and has its magnetic axis (1) lying in a plane in which the array lies, (2) extending along the circumference of the array, and (3) oriented so that each magnet continuously magnetically attracts the next adjacent magnets in the array, for controlling flow of matter through said lumen.

11. Prosthetic apparatus for implanting in a patient's body to urge a lumen in the body toward a closed position comprising:
    a plurality of more than two permanent magnets adapted for implanting in an annular array around the lumen; and
    means for keeping the magnets' positions in the array with each magnet occupying a respective segment of a circumference of the array and having its magnetic axis (1) extending along the circumference of the array, (2) lying in a plane in which the array lies, and (3) oriented so that each magnet continuously magnetically attracts the next adjacent magnets in the array, for controlling flow of matter through said lumen.

12. Prosthetic apparatus for implanting in a patient's body to urge a lumen in the body toward a closed position comprising:

a plurality of more than two permanent magnets adapted for implanting in an annular array around the lumen; and retaining structure that keeps each magnet at a respective position in the array with the magnetic axis of that magnet (1) lying in a plane in which the array lies, (2) aligned along a circumference of the array at that position, and (3) oriented so that each magnet continuously magnetically attracts the next adjacent magnets in the array, for controlling flow of matter through said lumen.

* * * * *